United States Patent [19]

Takehira et al.

[11] 4,400,544

[45] Aug. 23, 1983

[54] METHOD FOR THE PREPARATION OF CYCLOHEXANONE

[75] Inventors: Katsuomi Takehira, Yatabe; Toshio Ishikawa, Tokyo; Takashi Hayakawa, Yatabe; Juichi Imamura, Chofu, all of Japan

[73] Assignee: Director-General of the Agency of Industrial Science and Technology, Tokyo, Japan

[21] Appl. No.: 341,758

[22] Filed: Jan. 22, 1982

[30] Foreign Application Priority Data

Mar. 20, 1981 [JP] Japan .................................. 56-42114

[51] Int. Cl.$^3$ .............................................. C07C 45/34
[52] U.S. Cl. ................................................... 568/360
[58] Field of Search .............. 568/385, 342, 311, 338, 568/360

[56] References Cited

U.S. PATENT DOCUMENTS

| | | | |
|---|---|---|---|
| 3,340,304 | 9/1967 | Schulz et al. | 568/360 |
| 3,370,073 | 2/1968 | Clement et al. | 568/338 |
| 3,391,190 | 7/1968 | Kilsheimer et al. | 568/360 |
| 3,410,807 | 11/1968 | Lloyd | 252/429 R |
| 3,927,108 | 12/1975 | van de Moesdyk et al. | 568/342 |
| 4,271,320 | 6/1981 | Takitah et al. | 568/360 |

*Primary Examiner*—James H. Reamer
*Attorney, Agent, or Firm*—Brisebois & Kruger

[57] ABSTRACT

The invention provides an efficient method for the preparation of cyclohexanone by the liquid-phase oxidation of cyclohexene in the presence of a catalyst system. The rate of conversion of the cyclohexene and the yield of cyclohexanone are unexpectedly increased when the reaction mixture brought into contact with oxygen or air contains a limited amount of an aliphatic alcohol having 2–10 carbon atoms in a molecule such as ethyl alcohol with the catalyst system composed of a palladium compound, e.g. $PdCl_2$, and at least one co-catalytic ingredient which is a copper compound or iron compound such as $CuCl_2$ or $FeCl_3$. The influence of benzene or cyclohexane admixed in the reaction mixture was studied to indicate no adverse effects or even better results in the reaction giving further advantages of the process in which the starting cyclohexene need not be purified and can be used as prepared by the partial hydrogenation of benzene or partial dehydrogenation of cyclohexane.

7 Claims, No Drawings

METHOD FOR THE PREPARATION OF CYCLOHEXANONE

BACKGROUND OF THE INVENTION

The present invention relates to a method for the preparation of cyclohexanone or, more particularly, to a method for the preparation of cyclohexanone by the oxidation of cyclohexene in the liquid phase with molecular oxygen in the presence of a catalyst.

Cyclohexanone is a very useful organic compound in chemical industry, for example, as the starting material of the monomers of nylons and polyesters and as the intermediate for the synthesis of various kinds of useful derivatives by virtue of the high reactivity thereof.

Along with the traditional processes for the preparation of cyclohexanone by the catalytic reduction of phenol and the catalytic dehydrogenation or oxidation of cyclohexanol, the currently practiced process therefor is the air-oxidation of cyclohexane in the liquid phase. This process is, however, very unsatisfactory from the standpoint of the efficiency of the process.

For example, the cyclohexanone product formed in the liquid phase is more susceptible to the oxidation under the manufacturing conditions of the autoxidation than the cyclohexane as the starting reactant so that the conversion of the cyclohexane cannot be sufficiently high rarely to exceed 7 to 8% since otherwise the cyclohexanone once formed in the liquid phase is lost by the further oxidation.

In addition, the selectivity of the reaction, i.e. the proportion of the consumed starting reactant converted to the desired product, is also unsatisfactory and usually in the range of 70 to 80% even when calculated as the total value for cyclohexanone and cyclohexanol, which latter can be converted to the desired cyclohexanone by undertaking the catalytic dehydrogenation.

Various attempts have been made to enhance the effeciency of the above process, in particular, as directed to the improvement of the catalyst used in the reaction but with no noticeable success due to the high reactivity of cyclohexanone.

Accordingly, it has been eagerly desired to develop a novel and efficient method for the industrial preparation of cyclohexanone.

SUMMARY OF THE INVENTION

It is therefore an object of the present invention to provide a novel and efficient method for the industrial preparation of cyclohexanone free from the above mentioned problems of insufficient efficiency in the prior art processes.

The starting reactant in the method of the present invention is cyclohexene which is obtained by the partial hydrogenation of benzene or by the partial dehydrogenation of cyclohexane and the method of the present invention for the preparation of cyclohexanone comprises contacting cyclohexene in a reaction mixture containing an aliphatic alcohol having 2 to 10 carbon atoms in a molecule in the liquid phase with molecular oxygen in the presence of a catalyst system composed of a palladium compound as the main ingredient and at least one compound selected from the group consisting of copper compounds and iron compounds as the co-catalytic ingredient.

It has been further unexpectedly discovered that the efficiency of the above process is further improved when the liquid reaction mixture contains a limited amount of benzene and/or cyclohexane owing to the simplified preparation of the starting cyclohexene omitting the step of purification after the partial hydrogenation of benzene or partial dehydrogenation of cyclohexane as the precursor of cyclohexene.

DETAILED DESCRIPTION OF THE PREFERRED EMBODIMENTS

It is known that cyclohexanone is obtained by the liquid-phase oxidation of cyclohexene when the reaction is carried out in the presence of a catalyst system composed of palladium chloride, copper chloride and aqueous hydrochloric acid (see, for example, Shokubai (Catalyst), volume 10, page 24 (1968)). This method as reported in the above mentioned literature is, however, not of value as an industrial process due to the rapid deactivation of the catalyst system, presumably, by the loss of the power of the copper ingredient for the re-oxidation of the palladium ingredient along with the complex formation of cyclohexene with the copper salt.

Therefore, the inventors' efforts have been directed to the solution of the above problem of the deactivation of the catalyst system and unexpectedly arrived at a discovery that the addition of an aliphatic alcohol to the reaction mixture is effective in preventing the deactivation of the catalyst system leading to the establishment of the above described inventive method, according to which the catalyst system composed of a palladium compound and at least one of copper compounds and iron compounds can lastingly retain its high activity and high selectivity to give the desired cyclohexanone in a remarkably high yield.

The compounds of palladium, copper and iron of which the catalyst system used in the inventive method is composed are not particularly limitative including inorganic salts and organic complex compounds. Preferred compounds are, however, halogen compounds or, more preferably, chlorides of these elements exemplified by palladium chloride, copper(I) chloride, copper(II) chloride, iron(II) chloride and iron(III) chloride in respect of the reactivity of the reactants. In respect of the valency state of the copper or iron compound, copper(II) or iron(III) compounds are preferred although copper(I) or iron(II) compounds can give substantially the same results since they are readily oxidized into their higher valency states under the conditions of the reaction.

In particular, it is advisable that these salts are introduced into the reaction mixture in the form of their crystalline form with water of crystallization in view of the increased solubility of these salts in the reaction mixture containing a small amount of water. Thus, the presence of a small amount of water in the reaction mixture is advantageous to accelerate the reaction when the content of water is in the range not to exceed 15% by volume based on the total volume of the reaction mixture.

The aliphatic alcohol to form the reaction mixture with the cyclohexene as the starting reactant should desirably have 2 to 10 carbon atoms in a molecule. Methyl alcohol is less preferred. The molecular structure of these alcohols is not particularly limitative provided that the alcohol is liquid under the conditions of the reaction temperature and pressure as described below including linear-chain and branched-chain alcohols and primary, secondary and tertiary alcohols. Preferred aliphatic alcohols are the primary alcohols having from 2 to 5 carbon atoms in a molecule exemplified by ethyl alcohol, propyl alcohol, butyl alcohol, isobutyl alcohol and pentyl alcohol. These alcohols are used as such as the diluent of cyclohexene as the starting reactant in the reaction mixture although small volumes of other solvents miscible with the alcohol and the reactant may be contained in the reaction mixture.

The content of the aliphatic alcohol in the reaction mixture is of importance in the inventive method and the proportion of cyclohexene to the alcohol should be in the range from 1:0.05 to 1:100 by volume or, preferably, from 1:0.5 to 1:10 by volume. When the amount of the alcohol is smaller than above, the velocity of the oxidation reaction is decreased while a larger amount of the alcohol is undesirable from the viewpoint of the decreased productivity of the process due to the excessive dilution of the reactant. When no aliphatic alcohol is added to the reaction mixture, substantially no reaction takes place for the oxidation of cyclohexene to cyclohexanone.

The amount of the catalyst system in the reaction mixture should be such that the reaction mixture contains from 0.001 to 10% by weight or, preferably, from 0.01 to 1% by weight of the palladium compound and from 0.01 to 20% by weight or, preferably, from 0.1 to 10% by weight of the copper and/or iron compounds.

The oxidation reaction of the inventive method is performed by bringing the liquid reaction mixture comprising cyclohexene, the aliphatic alcohol and the catalyst system dissolved or dispersed therein into contact with an oxidizing gas containing molecular oxygen which may be either pure oxygen gas or an oxygen-containing gas such as air. The gas-liquid contacting can be performed in any conventional method known in the chemical engineering such as bubbling of the gas into the liquid.

The pressure of the oxidizing gas should be in the range from atmospheric to about 30 kg/cm$^2$ although higher pressures may be used though with some disadvantages in the use of a reaction vessel of increased pressure resistance despite the relatively small additional advantages obtained by the use of such an extremely high pressure. The reaction temperature should be in the range from room temperature to about 200° C. or, preferably, from about 40° to about 150° C. since lower temperatures are undesirable due to the decreased velocity of the reaction while higher temperatures are undesirable due to the increased velocity of side reactions as well as increased loss of the aliphatic alcohol from the reaction mixture.

As is mentioned before, cyclohexene is industrially obtained by the partial hydrogenation of benzene or partial dehydrogenation of cyclohexane so that it is very important to establish the influence of benzene and/or cyclohexane in the reaction mixture on the oxidation reaction of cyclohexene according to the inventive method. In this regard, the inventors have undertaken experimental investigations by admixing benzene and/or cyclohexane to the reaction mixture and unexpectedly discovered that the addition of benzene and/or cyclohexane to the reaction mixture has no adverse effect on the oxidation reaction of cyclohexene or gives even better results notwithstanding the further dilution of the starting cyclohexene.

It is of course that the amount of benzene and/or cyclohexane in the reaction mixture should be limited within a limit because excessive dilution of the reactant is in any way undesirable. In this respect, the amount of benzene and/or cyclohexane should be 10 times by volume or smaller based on the amount of cyclohexene in the reaction mixture. At any rate, the possibility of using cyclohexene containing a considerable amount of benzene and/or cyclohexane can afford a great advantage from the practical viewpoint since complete purification of cyclohexene by distillation from a mixture with benzene and/or cyclohexane is further a difficult matter in view of the proximity of their boiling points.

In the following, examples of the inventive method and comparative examples are given to illustrate the invention in further detail.

EXAMPLE 1

(Experiments No. 1 to No. 24)

A reaction mixture was prepared in a glass vessel of 100 ml capacity by admixing 10 ml of cyclohexene and 20 ml of an aliphatic alcohol incicated in Table 1 below with addition of 0.6 m mole of palladium chloride PdCl$_2$ and 3.0 m moles of a co-catalytic ingredient indicated in the table, the catalytic ingredients being dissolved in the mixture. The reaction was carried out by agitating the reaction mixture at 60° C. under an oxygen pressure of 860 mmHg for 2 hours during which the oxygen gas was absorbed by the reaction mixture.

The kinds of the co-catalytic ingredient and the alcohol, conversion of cyclohexene in %, yield of cyclohexanone in % based on the amount of cyclohexene taken and selectivity of the cyclohexanone formation calculated from the results of the gas chromatographic analysis are given in Table 1.

The experiments were conducted with various combinations of the co-catalytic ingredients and the aliphatic alcohols. As is clear from the results shown in the table, satisfactory results were obtained only when the iron or copper compound as the co-catalytic ingredient was combined with an aliphatic alcohol having from 2 to 10 carbon atoms in a molecule. When the ethyl or higher alcohol was replaced with methyl alcohol (Experiment No. 23) or the iron or copper salt was replaced with nickel chloride (Experiment No. 24), substantially no reaction took place or the activity of the catalyst system and the selectivity of the reaction were quite unsatisfactory. Among the iron and copper compounds tested as the co-catalytic ingredient, the halides gave better results than nitrates and chlorides were preferable to the corresponding bromides.

TABLE 1

| Experiment No. | Co-catalytic ingredient | Aliphatic alcohol | Conversion of cyclohexene, % | Yield of cyclohexanone, % | Selectivity of cyclohexanone, % |
|---|---|---|---|---|---|
| 1 | | Ethyl | 15.6[1] | 10.5 | 67.3 |
| 2 | | n-Propyl | 16.1 | 10.8 | 67.2 |
| 3 | | n-Butyl | 17.7 | 9.9 | 55.6 |
| 4 | | n-Pentyl | 17.8 | 9.5 | 53.2 |
| 5 | | n-Hexyl | 18.7 | 7.5 | 40.0 |

TABLE 1-continued

| Experiment No. | Co-catalytic ingredient | Aliphatic alcohol | Conversion of cyclohexene, % | Yield of cyclohexanone, % | Selectivity of cyclohexanone, % |
|---|---|---|---|---|---|
| 6 | FeCl$_3$.6H$_2$O | n-Octyl | 13.4 | 6.2 | 46.3 |
| 7 | | 2-Methyl-1-propyl | 18.8 | 8.5 | 45.1 |
| 8 | | Isopropyl | 12.0 | 4.8 | 40.0 |
| 9 | | 2-Butyl | 10.8 | 4.2 | 39.0 |
| 10 | | tert-Butyl | 11.1 | 5.0 | 45.0 |
| 11 | | Ethyl | 13.9[2] | 10.8 | 77.8 |
| 12 | | n-Propyl | 19.1 | 11.0 | 57.5 |
| 13 | | n-Butyl | 20.4 | 10.0 | 49.0 |
| 14 | | n-Pentyl | 17.4 | 7.1 | 40.7 |
| 15 | | n-Hexyl | 11.9 | 4.5 | 38.0 |
| 16 | CuCl$_2$.2H$_2$O | n-Octyl | 12.4 | 4.1 | 33.0 |
| 17 | | 2-Methyl-1-propyl | 7.0 | 4.9 | 69.4 |
| 18 | | Isopropyl | 5.6 | 2.9 | 51.3 |
| 19 | | 2-Butyl | 4.3 | 1.5 | 35.5 |
| 20 | | tert-Butyl | 7.1 | 2.6 | 36.8 |
| 21 | Fe(NO$_3$)$_3$.9H$_2$O | Ethyl | 9.3[3] | 2.9 | 31.3 |
| 22 | CuBr$_2$ | Ethyl | 5.5[4] | 2.5 | 46.0 |
| 23 | FeCl$_3$.6H$_2$O | Methyl | 0 | 0 | — |
| 24 | NiCl$_2$.6H$_2$O | Ethyl | 7.7[5] | 0.28 | 3.6 |

Oxygen absorption:
[1] 12.2 m moles
[2] 8.5 m moles
[3] 4.1 m moles
[4] 2.7 m moles
[5] 0.96 m mole

EXAMPLE 2

(Experiments No. 25 to No. 30)

In a similar manner to Example 1, a reaction mixture was prepared in a glass vessel of 100 ml capacity by admixing 10 ml of cyclohexene with ethyl alcohol and benzene and/or cyclohexane as well as palladium chloride as the main catalytic ingredient and iron chloride or copper chloride as the co-catalytic ingredient. The amounts of these ingredients admixed with the cyclohexene are shown in Table 2 below.

The oxidation reaction was conducted at 60° C. under an oxygen pressure of 860 mmHg with agitation of the reaction mixture and the volume of the oxygen absorption was measured periodically at 30 minutes intervals along with sampling of a small portion of the reaction mixture, of which the gas chromatographic analysis was undertaken. The results of the oxygen absorption measurements and the conversion of cyclohexene, yield of cyclohexanone and selectivity of cyclohexanone formation calculated from the results of the gas chromatography are shown in the table. As is clear from the comparison of the results shown in Tables 1 and 2, the addition of benzene and/or cyclohexane has little influences on the oxidation reaction of cyclohexene into the desired cyclohexanone.

TABLE 2

| Experiment No. | Ethyl alcohol, ml | Benzene (B) or cyclohexane (C), ml | PdCl$_2$, m moles | FeCl$_3$.6H$_2$O (Fe) or CuCl$_2$.2H$_2$O (Cu), m moles | Reaction time, minutes | Oxygen absorption, m moles | Conversion of cyclohexene, % | Yield of cyclohexanone, % | Selectivity of cyclohexanone, % |
|---|---|---|---|---|---|---|---|---|---|
| 25 | 20 | (B) 10 | 0.8 | (Fe) 4.0 | 30 | 2.1 | 6.1 | 2.1 | 34.7 |
| | | | | | 60 | 5.7 | 11.9 | 5.4 | 45.6 |
| | | | | | 90 | 8.7 | 15.4 | 8.3 | 54.1 |
| | | | | | 120 | 11.0 | 18.2 | 10.7 | 59.0 |
| 26 | 20 | (B) 10 (C) 10 | 1.0 | (Fe) 5.0 | 30 | 1.7 | 2.0 | 1.8 | 90.0 |
| | | | | | 60 | 4.3 | 4.6 | 3.4 | 73.9 |
| | | | | | 90 | 6.5 | 9.1 | 6.3 | 68.7 |
| | | | | | 120 | 8.9 | 11.0 | 8.8 | 79.4 |
| 27 | 20 | (B) 10 | 0.8 | (Cu) 4.0 | 30 | 1.2 | 3.2 | 2.7 | 83.5 |
| | | | | | 60 | 3.6 | 5.5 | 4.8 | 86.2 |
| | | | | | 90 | 5.6 | 7.7 | 7.6 | 90.0 |
| | | | | | 120 | 7.5 | 12.5 | 10.1 | 81.3 |
| 28 | 20 | (B) 10 (C) 10 | 1.0 | (Cu) 5.0 | 30 | 0.9 | 3.8 | 1.9 | 50.0 |
| | | | | | 60 | 2.3 | 5.7 | 3.5 | 60.7 |
| | | | | | 90 | 3.7 | 9.6 | 5.1 | 53.2 |
| | | | | | 120 | 5.0 | 10.0 | 7.5 | 74.3 |
| 29 | 5 | (B) 15 | 0.6 | (Fe) 3.0 | 30 | 0.96 | 3.4 | 1.3 | 37.6 |
| | | | | | 60 | 2.1 | 5.3 | 2.6 | 49.1 |
| | | | | | 90 | 3.5 | 7.1 | 3.8 | 53.2 |
| | | | | | 120 | 4.7 | 8.7 | 4.9 | 55.9 |
| 30 | — | (C) 15 | 0.6 | (Cu) 3.0 | 120 | 3.7 | 3.4 | 2.0 | 60.3 |

What is claimed is:

1. A method for the preparation of cyclohexanone by liquid-phase oxidation of cyclohexene which comprises reacting, at a temperature from room temperature to about 200° C. and at a pressure from atmospheric pressure to about 30 Kg/cm², a liquid reaction mixture comprising benzene and/or cyclohexane, and cyclohexene and an aliphatic alcohol having from 2 to 10 carbon atoms in a molecule with an oxidizing gas in the presence of 0.001 to 10% by weight of palladium chloride as a main catalytic ingredient and 0.01 to 20% by weight of a chloride of copper or iron as a co-catalytic ingredient, based on the amount of cyclohexene in the reaction mixture, and wherein the amount of benzene and/or cyclohexane does not exceed 10 times by volume the amount of the cyclohexene in the reaction mixture.

2. The method of claim 1 wherein the reaction temperature is from about 40° C. to about 200° C.

3. The method as claimed in claim 1 wherein the amount of the aliphatic alcohol is in the range from 5% to 100 times by volume based on the amount of the cyclohexene in the reaction mixture.

4. The method as claimed in claim 1 wherein the oxidizing gas is oxygen gas or air.

5. The method as claimed in claim 1 wherein the aliphatic alcohol is a primary alcohol having from 2 to 5 carbon atoms in a molecule.

6. The method as claimed in claim 5 wherein the aliphatic alcohol is ethyl alcohol.

7. The method as claimed in claim 1 wherein the liquid reaction mixture further comprises water in an amount not to exceed 15% by volume based on the total volume of the reaction mixture.

* * * * *